United States Patent
Weinberg et al.

(10) Patent No.: US 6,787,527 B1
(45) Date of Patent: Sep. 7, 2004

(54) METHODS OF PREVENTING AND TREATING HIV INFECTION

(75) Inventors: J. Brice Weinberg, Durham, NC (US); Derrick L. Sauls, Raleigh, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 08/339,215

(22) Filed: Nov. 10, 1994

(51) Int. Cl.⁷ .............................................. A62K 31/70
(52) U.S. Cl. ...................................................... 514/52
(58) Field of Search .......................................... 514/52

(56) References Cited

FOREIGN PATENT DOCUMENTS

| AU | 54534/90 | | 11/1990 | .......... | A61K/31/68 |
|---|---|---|---|---|---|
| DE | 1467743 | * | 12/1968 | | |
| DE | 2005757 | * | 9/1970 | .......... | A61K/27/00 |
| FR | 2558062 | * | 7/1985 | .......... | A61K/31/52 |
| GB | 1076670 | * | 7/1967 | ............ | A61K/3/44 |
| GB | 1178984 | * | 1/1970 | .......... | A61K/25/00 |
| JP | 0113721 | * | 9/1980 | .......... | A61K/31/70 |

OTHER PUBLICATIONS

Stryer Ed, Biochemisty 2 nd Ed, 1981 Freeman & Co pp 419–422.*
Miller et al, 1986, PNAS, Vol 83 pp 2531–2535.*
Scientific American, Apr. 1991, pp 2116–2123 Trollais et al.*
Merch Index 10$^{th}$ Ed, 1983, # 9822.*

* cited by examiner

*Primary Examiner*—Russell Travers
(74) *Attorney, Agent, or Firm*—Nixon & Vanderhye P.C.

(57) ABSTRACT

The present invention relates, in general, to a method of preventing or treating human immunodeficiency virus (HIV) infection, and in particular, to a method of preventing or treating HIV infection using a cobalamin. The invention further relates to compositions suitable for use in such a method.

4 Claims, 5 Drawing Sheets

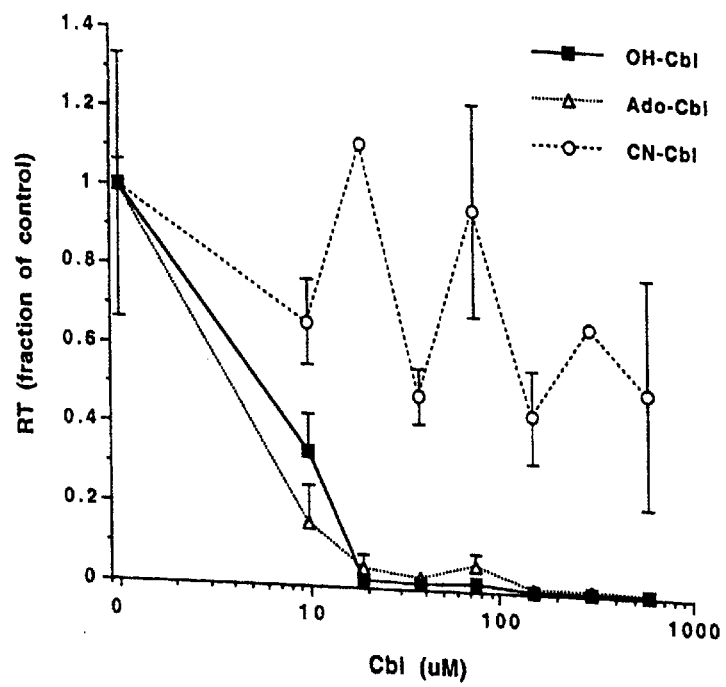
Figure 1A. Inhibition of HIV-1-BaL infection in monocytes by OH-Cbl and Ado-Cbl (but not by CN-Cbl).

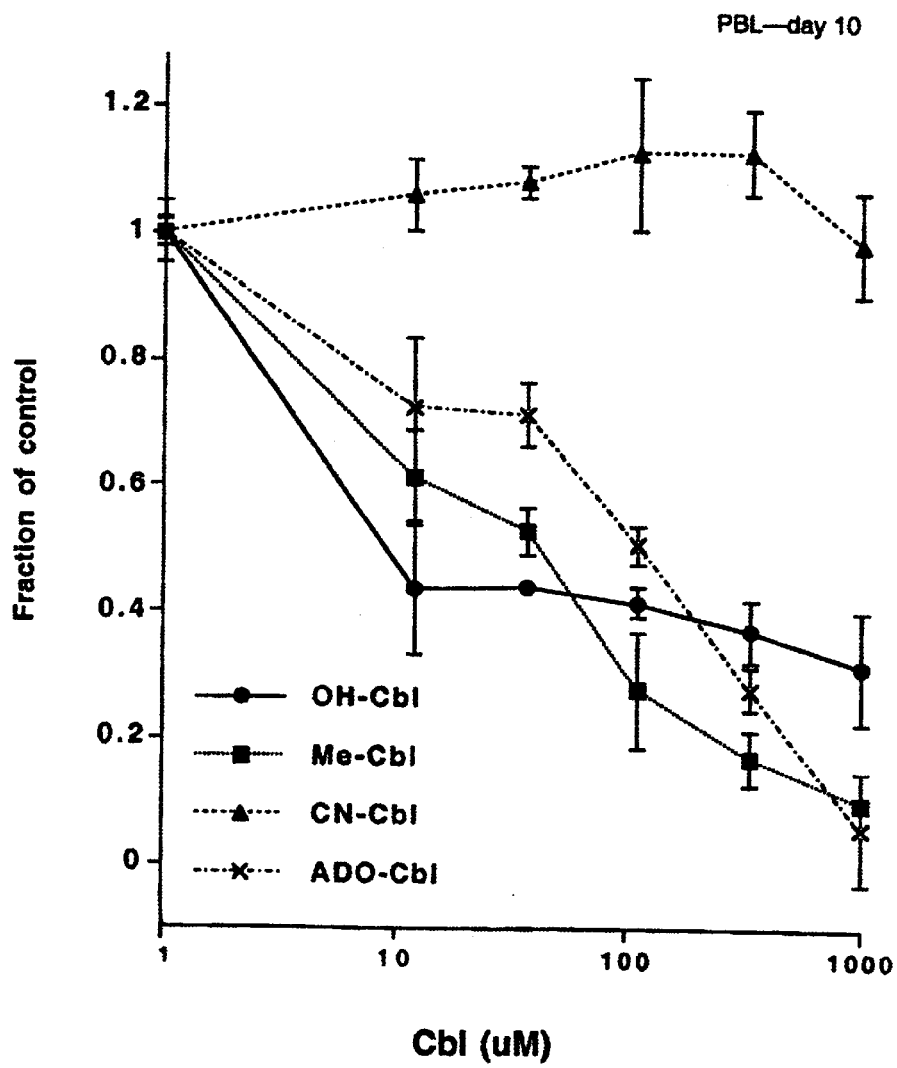
Figure 1B. Inhibition of HIV-1-IIIB infection of PBL by OH-Cbl, Me-Cbl, and Ado-Cbl (but not CN-Cbl) (day 10). PBL signifies peripheral blood lymphocytes.

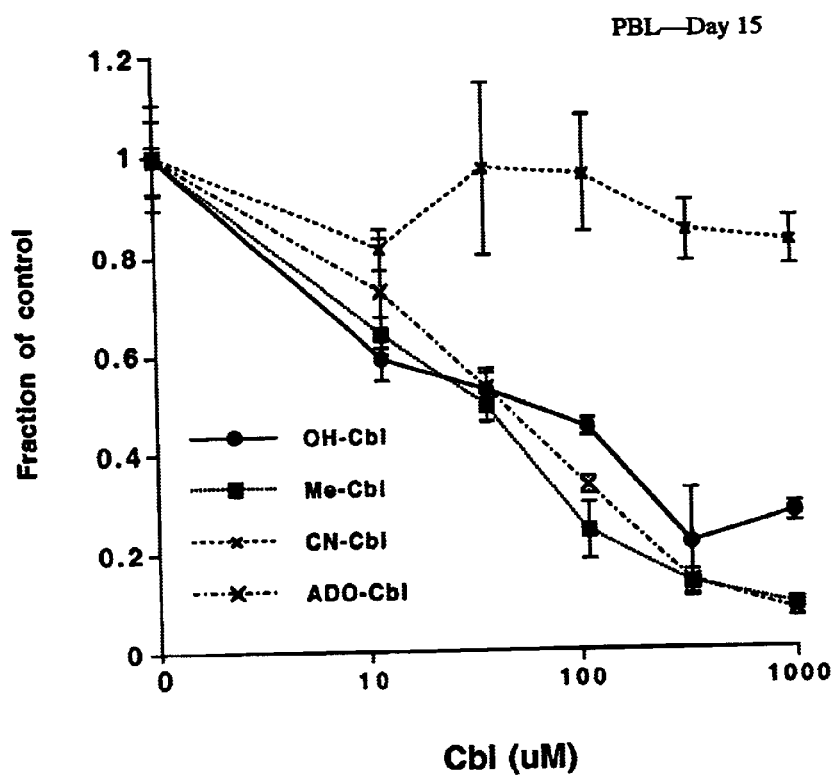
Figure 1C. Inhibition of HIV-1-IIIB infection of PBL by OH-Cbl, Me-Cbl, and Ado-Cbl (but not CN-Cbl) (day 15). PBL signifies peripheral blood lymphocytes.

Figure 2A. Lack of inhibition of CD4 binding to gp120$_{IIIB}$ by cobalamins.

Figure 2B. Lack of inhibition of CD4 binding to gp120$_{MN}$ by cobalamins.

METHODS OF PREVENTING AND TREATING HIV INFECTION

This invention was made with Government support under Grant No. AR39162 awarded by the National Institutes of Health. The Government has certain rights in this invention.

FIELD OF THE INVENTION

The present invention relates, in general, to a method of preventing or treating human immunodeficiency virus (HIV) infection, and in particular, to a method of preventing or treating HIV infection using a cobalamin. The invention further relates to compositions suitable for use in such a method.

BACKGROUND

HIV-1 causes the disease designated acquired immunodeficiency syndrome (AIDS). HIV-1 infects both lymphocytes and mononuclear phagocytes. Many of the infection of lymphocytes results in cell death and thus in a severe depletion in lymphocyte number. Infected mononuclear phagocytes apparently do not die, but rather remain in tissues as reservoirs of the HIV-1. HIV-1 infected mononuclear phagocytes not only serve as reservoirs of the virus, but they also are thought to elaborate toxic materials that cause (or contribute to) problems such as HIV-1-associated neurodegenerative disease. Also, HIV-1 infection of mononuclear phagocytes reduces the ability of these cells to perform their normal host defense functions, such as mediation of resistance to infection by intracellular organisms (e.g. *Cryptococcus neoformans*) and mediation of resistance to tumor development and growth.

Productive cellular infection with HIV-1 is controlled by various viral and host cell factors (Greene, New Eng. J. Med. 324:308 (1991); Fauci, Ann. Int. Med. 114:678 (1991); Weinberg, Current Opin. Hematol. 1:138 (1993)). Although recent work has demonstrated that nitric oxide (NO) can exert an anti-viral effect on DNA viruses (Croen, J. Clin. Invest. 91:2446 (1993); Karupiah et al, Science 261:1445 (1993)), inhibition of HIV-1 infection by NO has not been reported. Phagocyte production of NO has, however, been observed. For example, human mononuclear phagocytes can, after appropriate stimulation, produce low levels of NO (Denis, J. Leuk. Biol. 49:380 (1991); Zembala et al, Eur. J. Immunol. 24:435 (1994); Martin et al, J. Immunol. 150:3478 (1993); Pietraforte et al, J. Leuk. Biol. 55:175 (1994); Kolb et al, J. Biol. Chem. 269:9811 (1994); Hunt et al, Journal of Hepatology 14:146 (1992); Munoz-Fernandez et al, Immunol. Letters 33:35 (1992)). Further, Bukrinsky et al have shown that HIV-1 infected monocytes have increased production of NO in vitro (Bukrinsky et al, J. Exp. Med. in press (1994)) and Pietreforte and colleagues have reported that HIV-1 gp120 causes human monocytes to produce NO (Pietraforte et al, J. Leuk. Biol. 55:175 (1994)).

The present invention results from a series of experiments designed to study the role of NO on HIV-infection. Since NO binds to the cobalt of cobalamin, cobalamin derivatives were used in these experiments as potential quenchers of NO activity (Akaike et al, Eur. J. Pharmacol. 241:1 (1993); Rand et al, Eur. J. Pharmacol. 241:249 (1993); Rajanayagam et al, Br. J. Pharmacol. 108:3 (1993); Weinberg et al, Blood abstract in press (1994)). Surprisingly, it was observed that various cobalamin derivatives potently inhibited the ability of HIV to cause productive infection of human mononuclear phagocytes (monocytes (Mo) and peritoneal macrophages (Mac)) and normal blood lymphocytes (peripheral blood mononuclear cells (PBL)). The present invention thus provides a novel approach to the prevention and treatment of HIV infection that can be used alone or in combination with antiviral agents, such as reverse transcription inhibitors, currently in use.

SUMMARY OF THE INVENTION

The present invention relates to a method of inhibiting human immunodeficiency virus (HIV) infection of a cell comprising contacting the cell with an amount of a cobalamin sufficient to effect the inhibition.

Objects and advantages of the present invention will be clear from the description that follows.

BRIEF DESCRIPTION OF THE DRAWINGS

FIGS. 1A–1C: Effect of cyanocobalamin (CN-Cbl), hydroxocobalamin (OH-Cbl), and adencobalamin (Ado-Cbl) on HIV-1 infection of blood monocytes and lymphocytes. FIG. 1A. Effect of cobalamin derivatives on HIV-1-BaL infection of monocytes. FIG. 1B. Effect of cobalamin derivatives on HIV-1-IIIB infection of PBL (10 days). FIG. 1C. Effect of cobalamin derivatives on HIV-1-IIIB infection of PBL (15 days).

FIGS. 2A and 2B: Effect of CN-Cbl, OH-Cbl, Me-Cbl and Ado-Cbl on CD4-gp120 binding. FIG. 2A Gp120 from HIV-1-IIIB. FIG. 2B. Gp120 from HIV-1-MN.

DETAILED DESCRIPTION OF THE INVENTION

The present invention relates to a method of preventing and or treating HIV infection. More specifically, the invention relates to a method of inhibiting HIV infection of leukocytes (including peripheral blood lymphocytes, monocytes and tissue macrophages). The inhibition is effected using a cobalamin derivative. Cobalamins are important co-factors for different enzyme reactions, including methionine synthase (Me-Cbl) and methylmalonyl CoA synthase (Ado-Cbl) (Tefferi et al, Mayo Clinic Proc. 69:181 (1994); Hogenkamp, "The chemistry of cobalamins and related compounds". In: Babior BM, ed. Cobalamin. Biochemistry and pathophysiology. New York: John Wiley & Sons, 21 (1975)). In addition, cobalamins appear to bind nitric oxide (NO) and thereby modify its action in vitro and in vivo. Rand and Li, and Rajanayagam et al showed that OH-Cbl inhibited NO-mediated smooth muscle relaxation (Rand et al, Eur. J. Pharmacol. 241:249 (1993); Rajanayagam et al, Br. J. Pharmacol. 108:3 (1993)). Akaike and colleagues noted that Me-Cbl could inhibit NO mediated cytotoxicity of neural cells in vitro (Akaike et al, Eur. J. Pharmacol. 241:1 (1993)). The cobalt of OH-Cbl avidly binds NO (the cobalts of CN-Cbl, Me-Cbl, and Ado-Cbl, however, do not) (Weinberg et al, "Nitric oxidecobalamin interactions: implications regarding vitamin B12 deficiency states, submitted 1994; Nicolaou et al, Bio. Soc. Trans. 22:224 (1994); Nicolaou et al, Bio. Soc. Trans. 22:296 (1994); Ast et al, Bio. Soc. Trans. 22:217 (1994)). Nitrosocobalamin has a reduced ability to serve as an enzyme co-factors (Akaike et al, Eur. J. Pharmacol. 241:1 (1993); Rand et al, Eur. J. Pharmacol. 241:249 (1993); Rajanayagam et al, Br. J. Pharmacol. 108:3 (1993); Weinberg et al, Blood abstract in press (1994)).

Cobalamin derivatives suitable for use in the present method include the natural substances OH-Cbl, Ado-Cbl and Me-Cbl. CN-Cbl has little or no inhibitory effect in vitro.

Since CN-Cbl is converted in vivo to the natural substances, efficacy of CN-Cbl in vivo can not be ruled out.

The levels of cobalamins required for in vitro inhibition of HIV-1 infection are substantially higher than the physiological levels (normal human vitamin $B_{12}$ serum level ~200 to 600 pM). However, therapeutic doses of cobalamins are generally nontoxic. For example, OH-Cbl has been administered to humans in very high doses (5 to 7 grams by bolus intravenous infusion), with resultant serum levels in the $\mu M$ to mM levels, as a treatment or for cyanide poisoning (Forsyth et al, J. Toxicol. Clin. Toxicol. 31:277 (1993)). Side effects at such levels are minimal and include red-colored urine and transient high blood pressure (presumably because of cobalamin binding of NO). In view of the in vitro data presented herein, it is expected that HIV-1-infected patients can be treated (e.g. orally, intravenously or transmucosally) with doses of cobalamin (e.g. hydroxocobalamin) sufficient to achieve blood and tissue high enough levels to inhibit HIV-1 infection.

One skilled in the art can determine an appropriate treatment regimen, however, by way of example, it is noted that treatment can be effected using intravenous infusion of cobalamin for several days or for several hours followed by oral administration of the cobalamin. Alternatively, oral administration of cobalamin every 2 to 4 hours can be used to provide levels high enough to be effective.

Compositions suitable for use in the present invention include a cobalamin derivative as an active agent, together with a pharmaceutically acceptable carrier. The composition can take the form of a sterile injectable solution wherein the concentration of cobalamin can be in the range of 0.2M to 4.0M, 0.5M to 2.0M being preferred. The formulation can also take the form of an elixir suitable for oral administration (concentrations of cobalamin can be in the ranges set forth above). The composition can also be formulated in dosage unit form, for example, as a capsule, tablet, etc. Further, the formulation can take the form of a gel, lotion, cream, salve, foam or other form suitable for topical or mucosal administration (e.g. vaginal or rectal administration). The cobalamin derivative can be formulated with other anti-HIV agents including, for example, reverse transcriptase inhibitors such as Zidovudine, Didanosine or d4T.

The mechanism(s) by which cobalamins inhibit HIV-1 infection is not known. Although most cells express receptors for the cobalamin transport protein transcobalamin II (TC-II), the cell-specific effects described in the Examples for inhibition (inhibition in Mo, Mac, and Lym, but not established cell lines) could be related to differences in TC-II receptors, which receptors may be important. These receptors may serve as accessory "receptors" (in addition to CD-4) for viral GP-120. Saturating the receptors with TC-II-cobalamin would thus block this accessory receptor and inhibit infection. Differences in cellular TC-II-receptors among cell types might explain the observed cellular differences. Based on the results presented below, the inhibtion appears to be pretranscriptional, and not related to gp120-CD4 binding. Cobalamins may serve to "activate" cellular mechanisms of defence [e.g., IFN-α production (Francis et al, AIDS Res. Human Retroviruses 8:199 (1992))]. Alternatively, it is possible that the Cbl binds NO produced within or near infected cells, and, by some mechanism, inhibits productive HIV-1 infection. A mechanism involving NO in Lym may be unlikely since these cells produce little or no NO (Moncada et al, N. Eng. J. Med. 329:2002 (1993)). On the other hand, NO may serve to enhance HIV productive infection by activating N-F-cappa B (Lander et al, J. Immunol. 150:1509 (1993)). Cobalamins, by inhibiting NO, may inhibit transcription of HIV mRNA by reducing N-F-cappa B activation by NO.

In addition to being useful in inhibiting/preventing HIV infection of, for example, mononuclear phagocytes, it is also expected that the use of cobalamins in accordance with the present invention will be effective in treating neurological disorders associated with cobalamin deficiency (ie vitamin $B_{12}$ deficiency) in HIV-1 infected individuals. An appreciable percentage of individuals with HIV-1 infection have low blood levels of vitamin $B_{12}$, but not all show clinical evidence of vitamin evidence $B_{12}$ deficiency (Coodley, "Vitamins in HIV infection". In: Watson RR, ed. Nutrition and AIDS. New York: CRC Press, Inc., 89 (1994)). Aspects of neurological disorders and brain pathology seen in those with HIV-1 infection have similarities to those observed in vitamin $B_{12}$ deficient patients (not infected with HIV-1) with neurological disease (Petito et al, NEJM 312:874 (1935); Navia et al, Ann. Neurol. 19:517 (1986); Navia et al, Arc. Neurol. 19:525 (1986); Kieburtz et al, Arch. Neurol. 48:312 (1991)). Dawson et al have found that brain cells may overproduce NO in response to HIV-1 infection or to gp120, and that the locally produced NO might be directly cytotoxic to neural cells (Dawson et al, Proc. Natl. Acad. Sci. USA 90:3256 (1993)). Loco-regional NO production in the nervous system might also serve to modify cobalamins and to create a relative functional deficiency of vitamin $B_{12}$ in selected regions of the nervous system. Since cobalamins inhibit productive HIV-1 infection, vitamin $B_{12}$ deficiency might contribute to neuropathology and cause a local enhancement of HIV-1 productive infection. Administration of cobalamins in accordance with the present invention is thus expected to prevent/treat NO mediated neurotoxicity, as well as to inhibit HIV infection.

The selective advantage for cobalamin inhibition of HIV infection of mononuclear phagocytes over other cell types (lymphocytes) is advantageous. It is known that in vivo transmission of HIV between individuals involves transmission of restricted monocytotropic HIV strains to target mononuclear phagocytes. Cobalamins are especially effective at blocking transmission to mononuclear phagocytes.

Certain aspects of the present invention are described in greater detail in non-limiting Examples that follow.

EXAMPLE I

Experimental Details

Monocytes and lymphocytes were isolated and cultured as previously described (J. Exp. Med. 174:1477 (1991)). Briefly, monocytes were isolated by sequential ficoll-sodium diazotrate and Percoll gradients with subsequent adherence to cultureware plastic, and then cultured in Dulbecco's modified Eagle medium (GIBCO, Grand Islands, N.Y.) with 10% unheated human serum. Lymphocytes were from ficoll-sodium diazotrate gradients, and were cultured with anti-CD3/anti-CD28 antibody and subsequently IL-2. Reverse transcription (RT) was measured as described (Weinberg et al, J. Exp. Med. 174:1477 (1991)) using a phosphoimager device for quantification. Leukemia cell lines Jurkat, CEM, HL-60, and U937 were obtained from American Type Culture Collection (Rockville, Md.). The cells were cultured in RPMI-1640 with 10% fetal bovine serum (Hyclone, Logan, Utah). Cobalamins were obtained from Sigma Chemical Company (St. Louis, Mo.). The cobalamins had extremely low endotoxin content, as determined by Limulus amebocyte lysate testing (Whitaker Bioproducts, Walkerville, Md.). When tested as a 3 mM solution, the cobalamins had less than 0.25 EU/ml. Cobalamins were not toxic for Mo, Mac, Lym, and leukemia cell line cells, as determined by morphology under phase microscopy, Wright staining of methanol-fixed cells, trypan blue exclusion, and thymidine incorporation were carried out in accordance with standard techniques.

Monocytes

Monocytes were inoculated at time zero with HIV-1-Bal (Weinberg et al, J. Exp. Med. 174:1477 (1991)) (MOI ~0.1)and cultured with the designated cobalamin for 7–14 days. Supernatant medium RT was then measured (Weinberg et al, J. Exp. Med. 174:1477 (1991)). Results are provided as RT activity (mean±SEM of triplicates)and are derived from one experiment. These results are, however, similar to those observed seen in various other experiments.

PBL

PBL were inoculated with HIV-1-IIIB (MOI ~0.1) and cultured with the designated cobalamin for 15–25 days. Supernatant medium RT was then measured. Results are provided as RT activity (mean±SEM of triplicates) and are derived from one experiment. These results are, however, similar to those observed seen in various other experiments.

Leukemia cell lines

Cells of the T lymphoblast cell line Jurkat and CEM, the myeloblast cell line HL-60, and the monoblast cell line U937 were inoculated with HIV-1-IIIB (MOI ~0.1) and cultured for with the designated cobalamin for 10–20 days. Supernatant medium RT was then measured. Results are provided as RT activity (mean±SEM of triplicates) and are derived from one experiment. These results are, however, similar to those observed seen in various other experiments.

Results:

OH-Cbl, Me-Cbl, Ado-Cbl, and CN-Cbl were not toxic for Mo, Mac, PBL, or cells of the human leukemia cell lines Jurkat, CEM, HL-60, or U937 at concentrations $\leq 600$ $\mu$M. When added to the cultures of Mo, Mac, or PBL at the time of viral inoculation on day zero and left in throughout the culture period, there was potent inhibition of productive infection as judged by supernatant medium RT activity (see FIG. 1). Further evidence of the cobalamin inhibitory effect was derived from studies examining syncytium formation. Populations of monocytes not inoculated with virus were generally mononuclear, while those inoculated with HIV-1-BaL (MOI ~0.1) cultured (14 days) without OH-Cbl (67 $\mu$M) had numerous multinucleated giant cells (syncytium). Populations of HIV-1-inoculated monocytes cultured with OH-Cbl did not contain multinucleated giant cells (ie 100% inhibition of syncytium formation).

The concentration of cobalamin required for 50% inhibition ($IC_{50}$) was approximately 2 to 4 $\mu$M when asessed in mononuclear phagocytes and about 25 to 50 $\mu$M in normal PBL. CN-Cbl exhibited little or no inhibitory activity in all experiments using Mo, Mac, and PBL. While OH-Cbl, Me-Cbl, and Ado-Cbl inhibited HIV-1 infection of these "primary," normal leukocytes, these compounds did not inhibit infection of cells of the human T lymphoblast lines Jurkat and CEM, the myeloblastic line HL-60, or the monoblastic line U937.

OH-Cbl, Me-Cbl, and Ado-Cbl inhibited infection of Mo with the monocytotropic strains HIV-1-BaL or HIV-1-ADA (NIH AIDS Repository, Bethesda, Md.), or PBL with HIV-1-BaL or the lymphocytotropic strain HIV-1-IIIB (inhibition of RT up to 90%). If Mo were pretreated with 250 $\mu$M OH-Cbl for 24 hours, washed well and then inoculated with HIV-1-BaL, the OH-Cbl-treated cells were protected against HIV-1 infection (inhibition of RT by approximately 80%). If Mo were incubated simultaneously with 250 $\mu$M OH-Cbl and HIV-1 for 4 hours, washed, and then cultured for 10 days, there was no inhibition of HIV-1 infection. If, however, Mo were inoculated with HIV-1 and cultured for 6 days (a time at which they displayed multinucleated giant cell formation and RT production), washed thoroughly and then cultured with 250 $\mu$M OH-Cbl, there was no inhibition of the subsequent RT production.

To determine whether OH-Cbl would inhibit the ability of latently-infected leukemia cells to produce RT after stimulation with tumor necrosis factor (TNF) or phorbol myristate acetate (PMA), U1 (U937 monoblastic cell line with HIV-1 integrated provirus) cells (NIH AIDS Repository) and OM-10.1 cells (HL-60 myelobastic cell line with HIV-1 integrated provirus) (Dr. Clay Smith, Duke University, Durham, N.C.) were treated with 500 U/ml TNF or 80 nM PMA (with or without 250 $\mu$M OH-Cbl). OH-Cbl did not inhibit the expression of the induced viral RT. The inability of the cobalamins to inhibit HIV-1 production in previously-infected Mo and in latently-infected leukemia cells indicates that the cobalamins probably affect HIV-1 infection in the steps before transcription from integrated viral DNA.

EXAMPLE II

Experimental Details

Cobalamins were incubated with CD4 and gp120 from HIV-1-IIIB in wells of microtiter wells, and binding was assessed as previously described. Displayed are the means and standard errors of the means of triplicate samples. Serum from an HIV-1-infected person containing anti-gp120 antibody served as the "positive control".

Results

To determine whether cobalamins modified the binding of HIV-1 gp120 to CD4, the abilities of CN-Cbl, OH-Cbl, Me-Cbl, and Ado-Cbl to inhibit binding of recombinant CD4 with gp120 from HIV-1-IIIB or HIV-1-MN were tested (FIG. 2). No inhibition of binding was observed. Also, the cobalamins did not modify RT activity. If 1 to 1000 $\mu$M CN-Cbl, OH-Cbl, Me-Cbl and Ado-Cbl were added to cell-free medium containing RT, inhibition of RT activity was not observed.

All documents cited above are hereby incorporated in their entirety by reference.

One skilled in the art will appreciate from a reading of this disclosure that various changes in form and detail can be made without departing from the true scope of the invention.

What is claimed is:

1. A method of treating human immunodeficiency virus (HIV) infection in a subject in need of such treatment comprising administering to said subject an amount of hydroxocobalamin, methylcobalamin or adenocobalamin sufficient to effect said treatment.

2. The method according to claim 1 wherein hydroxocobalamin is administered.

3. A method of treating an HIV associated neurological disorder comprising administering to a patient in need of such treatment an amount of hydroxycobalamin, methylcobalamin or adenocobalamin sufficient to treat said disorder.

4. The method according to claim 3 wherein hydroxocobalamin is administered.

* * * * *